United States Patent
Liu et al.

(10) Patent No.: US 7,322,243 B2
(45) Date of Patent: Jan. 29, 2008

(54) ACOUSTIC WAVE ETCH RATE SENSOR SYSTEM

(75) Inventors: James Z T Liu, Belvidere, IL (US); Michael L. Rhodes, Richfield, MN (US); Aziz Rahman, Sharon, MA (US)

(73) Assignee: Honeywell International Inc., Morristown, NJ (US)

( * ) Notice: Subject to any disclaimer, the term of this patent is extended or adjusted under 35 U.S.C. 154(b) by 111 days.

(21) Appl. No.: 11/156,012

(22) Filed: Jun. 16, 2005

(65) Prior Publication Data

US 2006/0283249 A1 Dec. 21, 2006

(51) Int. Cl.
*G01H 13/00* (2006.01)
*G01N 17/04* (2006.01)

(52) U.S. Cl. .......... 73/579; 73/61.49; 422/53

(58) Field of Classification Search .......... 73/579, 73/61.49, 61.79; 422/53
See application file for complete search history.

(56) References Cited

U.S. PATENT DOCUMENTS

| | | | |
|---|---|---|---|
| 4,691,714 A | 9/1987 | Wong et al. | 128/738 |
| 4,782,332 A | 11/1988 | Cipris et al. | 340/603 |
| 4,792,791 A | 12/1988 | Cipris et al. | 340/603 |
| 5,208,162 A | 5/1993 | Osborne et al. | |
| 5,235,235 A | 8/1993 | Martin et al. | 310/313 D |
| 5,274,335 A | 12/1993 | Wang et al. | 324/689 |
| 5,301,643 A | 4/1994 | Garcyalny | 123/198 D |
| 5,336,396 A | 8/1994 | Shetley | 210/90 |
| 5,852,229 A * | 12/1998 | Josse et al. | 73/24.06 |
| 5,856,198 A * | 1/1999 | Joffe et al. | 436/100 |
| 5,869,763 A | 2/1999 | Vig et al. | 73/580 |
| 5,878,708 A | 3/1999 | Ruman | 123/196 M |

(Continued)

FOREIGN PATENT DOCUMENTS

JP 61028841 A 2/1986

(Continued)

OTHER PUBLICATIONS

B. Jakoby, M. Scherer, M. Buskies, H. Eisenschmid; *An Automotive Engine Oil Viscosity Sensor* IEEE Sensors Journal vol. 3 No. 5 Oct. 2003, pp. 562-568.

(Continued)

*Primary Examiner*—John E. Chapman
(74) *Attorney, Agent, or Firm*—Matthew F. Lambrinos; Kermit D. Lopez; Luis M. Ortiz (57) ABSTRACT

An acoustic wave sensor system for monitoring the etch rate or etch ability of a selective material has an acoustic wave sensing device having a piezoelectric substrate and at least one electrode coupled to the substrate for generating a propagating acoustic wave and for detecting changes in frequency or other propagation characteristics of the acoustic wave. A selective material is disposed on the substrate. Changes in propagation characteristics of the wave caused by etching of the selective material by an etchant can be analyzed to evaluate the etching rate or etch ability of the selective material. The sensing system can have a wireless sensing device which device is mountable in an oil filter system for monitoring the corrosion of the engine. The sensing device can be configured as BAW, SH-SAW, SH-APM, FPM devices or other acoustic wave devices.

18 Claims, 7 Drawing Sheets

U.S. PATENT DOCUMENTS

| | | | |
|---|---|---|---|
| 6,029,500 A * | 2/2000 | Tom | 73/31.05 |
| 6,044,332 A | 3/2000 | Korsah et al. | 702/76 |
| 6,076,406 A | 6/2000 | Blair et al. | 73/590 |
| 6,293,136 B1 | 9/2001 | Kim | 73/19.03 |
| 6,457,361 B1 * | 10/2002 | Takeuchi et al. | 73/580 |
| 6,508,100 B2 | 1/2003 | Berndorfer | 73/1.02 |
| 6,557,396 B2 | 5/2003 | Ismail et al. | 73/53.05 |
| 6,662,642 B2 * | 12/2003 | Breed et al. | 73/146 |
| 6,776,024 B2 | 8/2004 | Jakoby | 73/10 |
| 6,786,080 B2 | 9/2004 | Jakoby et al. | 73/54.04 |
| 6,799,458 B2 | 10/2004 | Ismail et al. | 73/304 C |
| 2002/0078752 A1 | 6/2002 | Braunling et al. | |
| 2003/0233864 A1* | 12/2003 | Rodier | 73/24.06 |
| 2004/0035398 A1 | 2/2004 | Klugl et al. | 123/456 |

FOREIGN PATENT DOCUMENTS

WO          WO 98/19156 A          5/1998

OTHER PUBLICATIONS

R.M. Lee, X.J. Zhang, J.M. Hammond; *A Remote Acoustic Engine Oil Quality Sensor* Dept. of Electrical & Computer Engineering, University of Maine, 1997 IEEE Ultrasonics Symposium, pp. 419-422.

X. Zhang; *An On-Board Automobile Engine Oil Quality Sensor* Thesis, The Graduate School University of Maine, Aug. 1998.

* cited by examiner

ACOUSTIC WAVE ETCH RATE SENSOR SYSTEM

TECHNICAL FIELD

Embodiments are generally related to sensing devices, systems and methods and, in particular to acoustic wave sensor devices, such as, for example, bulk acoustic wave (BAW) devices and sensors. Embodiments are additionally related to sensors for sensing the chemical etchability of materials exposed to etching solutions or etchants. Additionally, embodiments are related to etch rate sensors which can be utilized in automotive or other applications for monitoring corrosion caused by exposure to degraded oil or other corrosive etchants.

BACKGROUND

Acoustic wave sensors are utilized in a variety of sensing applications, such as, for example, temperature and/or pressure sensing devices and systems. Acoustic wave devices have been in commercial use for over sixty years. Although the telecommunications industry is the largest user of acoustic wave devices, they are also used for sensor applications, such as in chemical vapor detection. Acoustic wave sensors are so named because they use a mechanical, or acoustic, wave as the sensing mechanism. As the acoustic wave propagates through or on the surface of the material, any changes to the characteristics of the propagation path affect the velocity and/or amplitude of the wave.

Changes in acoustic wave characteristics can be monitored by measuring the frequency or phase characteristics of the sensor and can then be correlated to the corresponding physical quantity or chemical quantity that is being measured. Virtually all acoustic wave devices and sensors utilize a piezoelectric crystal to generate the acoustic wave. Three mechanisms can contribute to acoustic wave sensor response, i.e., mass-loading, visco-elastic and acousto-electric effect. The mass-loading of chemicals alters the frequency, amplitude, and phase and Q value of such sensors. Most acoustic wave chemical detection sensors, for example, rely on the mass sensitivity of the sensor in conjunction with a chemically selective coating that absorbs the vapors of interest resulting in an increased mass loading of the SAW sensor. Examples of acoustic wave sensors include acoustic wave detection devices, which are utilized to detect the presence of substances, such as chemicals, or environmental conditions such as temperature and pressure.

An acoustical or acoustic wave (e.g., SAW/BAW) device acting as a sensor can provide a highly sensitive detection mechanism due to the high sensitivity to surface loading and the low noise, which results from their intrinsic high Q factor. Surface acoustic wave (SAW/SH-SAW) and amplitude plate mode (APM/SH-APM) devices are typically fabricated using photolithographic techniques with comb-like interdigital transducers (IDTs) placed on a piezoelectric material. Surface acoustic wave devices may have a delay line, a filter or a resonator configuration. Bulk acoustic wave devices are typically fabricated using a vacuum plater, such as those made by CHA, Transat or Saunder. The choice of the electrode materials and the thickness of the electrode are controlled by filament temperature and total heating time. The size and shape of electrodes are defined by proper use of mask. Based on the foregoing, it can be appreciated that acoustic wave devices, such as a surface acoustic wave resonator (SAW-R), surface acoustic wave filter (SAW-filter), surface acoustic wave delay line (SAW-DL), surface transverse wave (STW), bulk acoustic wave (BAW), can be utilized in various sensing measurement applications.

One promising application for micro-sensors involves oil filter and oil quality monitoring. Diesel engines are particularly hard on oil because of oxidation from acidic combustion. As the oil wears, it oxidizes and undergoes a slow build-up of total acids number (TAN). A pH sensor is capable of direct measurement of TAN and an indirect measurement of total base number (TBN), providing an early warning of oil degradation due to oxidation and excess of water. The acids and water build-up is also related to the viscosity of the oil.

Low temperature start-ability, fuel economy, thinning or thickening effects at high and/or low temperatures, along with lubricity and oil film thickness in running automotive engines are all dependent upon viscosity. Frequency changes in viscosity have been utilized in conventional oil detection systems. The frequency changes caused by small changes in viscosity of highly viscous liquids, however, are very small.

Because of the highly viscous loading, the signal from a sensor oscillator is very "noisy" and the accuracy of such measurement systems is very poor. Moreover, such oscillators may cease oscillation due to the loss of the inductive properties of the resonator.

There is a need to provide a sensor system which can be utilized to monitor, in a sensitive manner, the etching effects of etchants, such as acids contained in oils. There is also a need to provide a sensor system which can monitor corrosion or degradation of engines or other devices caused by exposure to such etchants. It is believed that acoustic wave sensors may well be suited for such monitoring as indicated by the embodiments described herein.

BRIEF SUMMARY OF THE INVENTION

The following summary of the invention is provided to facilitate an understanding of some of the innovative features unique to the present invention and is not intended to be a full description. A full appreciation of the various aspects of the invention can be gained by taking the entire specification, claims, drawings, and abstract as a whole.

It is, therefore, one aspect of the present invention to provide for improved sensing devices and applications.

It is another aspect of the present invention to provide for an acoustic wave sensor for sensing chemical etch ability of a selective material exposed to an etchant.

It is a further aspect of the present invention to provide for an acoustic wave etch rate sensor, such as, for example, a bulk acoustic wave (BAW) device, which can be utilized in automotive applications (e.g. as a sensor for monitoring corrosion or degradation of engines caused by exposure to degraded oil or other corrosive etchants).

It is an additional aspect of the present invention to provide an acoustic wave etch rate sensor which is highly sensitive and reliable throughout the life-time of the sensor.

The aforementioned aspects of the invention and other objectives and advantages can now be achieved as described herein. Acoustic wave sensor systems and methods for monitoring the etch ability of a material exposed to an etchant are disclosed.

The sensor system generally includes an acoustic wave sensing device having a piezoelectric substrate and at least one electrode coupled to the substrate. The or each electrode is adapted and arranged such that the sensing device can generate an acoustic wave propagating in the device upon application of a voltage potential and can transform the propagating wave into an output response. The sensing device includes a material having a chemically reactivity with the etchant such that the selective material is etchable by the etchant. The sensing device provides an output response in which changes in frequency, phase or other propagation characteristics of the propagating wave caused by etching of the selective material can be analyzed to evaluate the etching rate or etch ability of the selective material.

The selective material can be a material having reduced chemical reactivity with the etchant such that reaction products produced at an etched surface of the selective material dissolve in the etchant. For example, in automotive applications in which the etchant is degraded engine oil, the reduced reactivity material could be iron (Fe), nickel (Ni), manganese (Mn), cobalt (Co), chromium (Cr), scandium (Sc), vanadium (V), titanium (Ti), zinc (Zn) or other transition metal elements. By utilizing a selective material having a reduced reactivity, the etched surface remains fresh during sensor operation, that is, the etched surface remains free from reaction products, unlike in conventional corrosivity sensors in which metal oxides or metal sulfides remain on the electrode surface reducing the active surface of the sensor. Since the sensing device has a fresh surface for new reactions, the sensing device has a high sensitivity and a linear frequency response throughout the life time of the sensor.

One or more of the electrodes can be at least partially formed from the selective material such that the electrode(s) can be etched by the etchant.

The sensing device can include at least one reflector for reflecting the propagating wave back to at least one electrode. Additionally or alternatively, at least one of the reflectors can be at least partially formed from the selective material such that the reflector(s) can be etched by the etchant.

The sensing device can include a layer disposed on the substrate and fabricated from the selective material. The layer or coating can be formed as a thin film or coating. The layer can be disposed on the substrate such that the layer covers the electrode(s) and/or reflector(s) and, if need be, protects the electrode(s) and/or reflector(s).

The electrode(s) and/or reflector(s) other than any of those fabricated from the selective material can be adapted and arranged so as to be unetchable by the etchant. To this end, the electrode(s) and/or reflector(s) can be fabricated from an inactive material such that the etchant is incapable of etching the electrode(s) and/or reflector(s). For example, in automotive applications in which the etchant is degraded engine oil, the inactive electrode(s) and/or reflector(s) could be fabricated from gold (Au) or platinum (Pt). Alternatively, the sensing device can be designed such that the etchant is unable to contact the electrode(s) and/or reflectors thereby rendering the electrode(s) and/or reflector(s) inactive. For example, the electrode(s) and/or reflector(s) can be coated with a protective layer, such as an insulating layer, to seal the electrode from the etchant or the sensing device can be arranged such that, in operation, only the selective material comes in contact with the etchant. Also, the piezoelectric substrate can be made from an inactive material so that the etchant is only capable of etching the selective material. For example, in the case of automotive applications in which the etchant is degraded engine oil, the substrate can be made inactive by using a quartz substrate.

The sensing device can be configured either as an acoustic wave resonator, an acoustic wave filter or as an acoustic wave delay line device.

The sensor system can include an oscillator circuit coupled to the sensing device such that the sensing device is part of a feedback loop of the oscillator circuit. A frequency counter can be connected to the oscillator circuit and can be controlled by a processor for measuring changes in the oscillation frequency or amplitude caused by etching of the selective material.

The sensor system can include one or a plurality of oscillator circuits for exciting simultaneous multiple modes in the sensing device. Each oscillator circuit can be coupled to the sensing device such that the sensing device is part of the feedback loop(s) of the circuit(s). Simultaneous excitation of the sensing device enables separation of mass change effects caused by etching of the selective material from temperature or other environmental effects such that the etch rate measurement can be accordingly compensated.

The sensor system can include an antenna which can be integrated in the sensing device for receiving an interrogation signal. The antenna can be coupled to each electrode such that the sensing device can transform the signal into the acoustic wave sensor and provide the output response to the antenna for transmission. By integrating the antenna into the sensing device, the sensing device is operable passively without the need for directly providing the sensing device with a power supply or oscillator. Furthermore, the sensor system can detect and monitor the etch rate of the selective material remotely.

The sensor system can include an interrogation unit for transmitting the interrogation signal and for receiving the response transmitted from the sensing device.

The sensing device can be configured as a bulk acoustic wave device, such as for example a thickness shear mode (TSM) resonator in which the piezoelectric substrate can consist of a quartz crystal substrate. A pair of electrodes can be located on opposite faces of the quartz substrate. One of the electrodes can be made chemically inactive whilst the other can be fabricated from the selective material. If a selective layer material is used, the selective layer can be disposed on one of the substrate faces. The selective layer can cover and, if need be, protect the electrode covered by the layer.

Alternatively, the sensing device can be configured as a surface acoustic wave device (SAW), such as for example, a shear mode surface acoustic wave mode device (SH-SAW), a shear mode acoustic plate mode device (SH-APM) or a flexi plate mode (FPM) device. In such devices, each electrode can be in the form of an interdigital transducer (IDT).

For example, when the sensing device is configured as a SAW, SH-APM, FPM or other type of resonator, the resonator can be configured as a two-port resonator, i.e., a filter, in which an input interdigital transducer (IDT) and an output IDT are formed on the substrate between a pair of reflectors. A selective layer can be disposed on the substrate or alternatively, one of the IDTs or reflectors can be made selective. The selective sensitive layer can cover and protect the electrodes and reflectors and/or can be disposed between the two IDTs.

Each reflector may comprise at least one metallic membrane, such as metallic stripe, if necessary made from the selective material, and formed on the substrate spaced from the IDT(s). Alternatively, the inactive reflector may comprise an edge of the substrate which edge is substantially perpendicular to the propagation path of the wave.

In one particular embodiment, the sensing device can be utilized in automotive applications to monitor engine wear caused by degraded engine oil corroding the engine. To this end, the selective material is chosen to have etching characteristics similar to, or the same as, the engine material. The sensing device can be mounted in the oil filter system with the engine oil in contact with the selective electrode, reflector or layer fabricated from the selective material. By utilizing the engine material or a similar material as the selective material in the sensing device mounted in the oil filter system, the sensing device is capable of providing an etch rate measurement which directly reflects the degree of corrosion of the engine by the oil.

BRIEF DESCRIPTION OF THE DRAWINGS

The accompanying figures, in which like reference numerals refer to identical or functionally-similar elements throughout the separate views and which are incorporated in and form a part of the specification, further illustrate the present invention and, together with the detailed description of the invention, serve to explain the principles of the present invention.

DETAILED DESCRIPTION OF THE INVENTION

The particular values and configurations discussed in these non-limiting examples can be varied and are cited merely to illustrate at least one embodiment of the present invention and are not intended to limit the scope of the invention.

Figure 1:
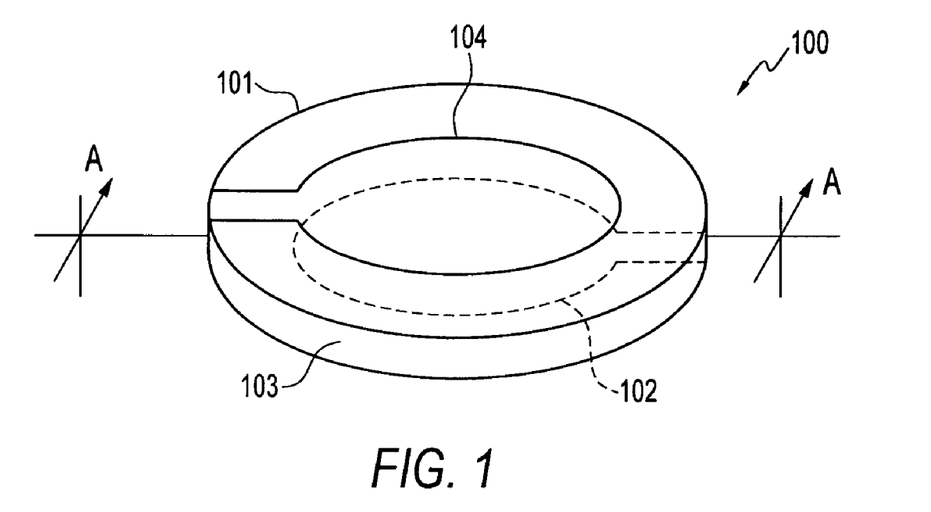
FIG. 1 illustrates a front perspective view of an acoustic wave sensing device of a sensor system for monitoring the etch rate of a material exposed to an etchant in accordance with a preferred embodiment.

Referring to FIG. 1 of the accompanying drawings, which illustrates a front perspective view of an acoustic wave sensing device of an sensor system for monitoring the etch rate of a material exposed to an etchant in accordance with a preferred embodiment, the sensor system 100 consists of an acoustic wave sensing device 101 having a piezo-electric substrate 103, and at least one electrode 102,104, coupled to the substrate. The or each electrode is adapted and arranged such that the sensing device can generate an acoustic wave propagating in the device upon application of a voltage potential and can transform the propagating wave into an output response.

A selective material 104, chosen to be selectively etchable by the etchant of interest, is disposed on the substrate. In this particular case, the selective material is in the form of a layer which layer can be a thin film or coating.

The detection mechanism of a selective coating utilized in an acoustic wave chemical etch rate sensor is dependent on the mass loading effect when exposed to measurands, such as the etchant.

Factors that influence the sensing device properties include physical/chemical properties of the selective coating such as for example film thickness, modulus, film morphology, and the interface or bonding between the film and substrate.

The selection of the selective coating or thin film material affects the sensing device selectivity, that is, the measured etch rate of the sensing device selective coating or thin film material compared to the etch rate of a reference material for a given etchant. Furthermore, the thin film fabrication process affects the sensing device response to the etchants and therefore contributes to selectivity. Whilst perfect selectivity for a single analyte is unattainable except for biological based thin films, adequate selectivity for a particular application is possible if the potential interferantes are known.

Figure 2:
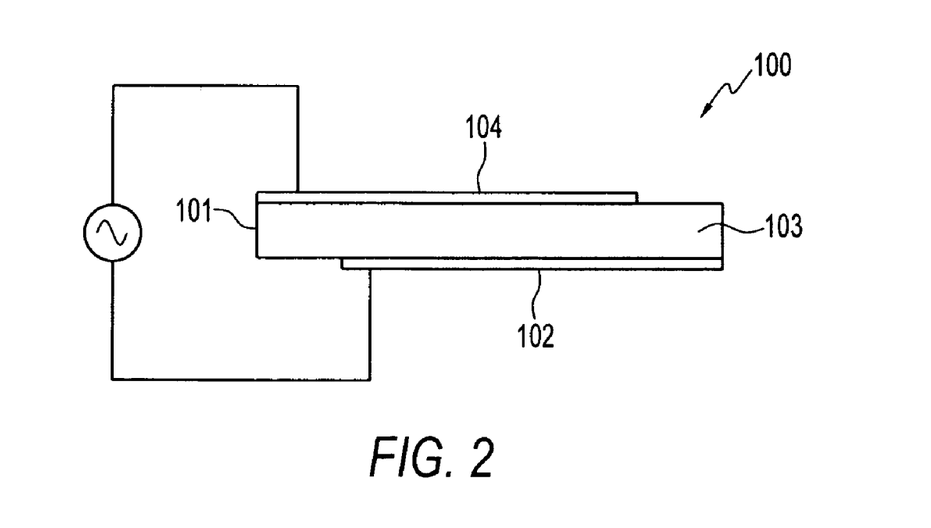
FIG. 2 illustrates a cross-sectional view taken along line A-A of the sensing device depicted in FIG. 1.

In this particular embodiment, the sensing device 101 is configured as a bulk acoustic wave device in the form of a thickness shear mode (TSM) resonator, in which a pair of electrodes 102, 104 are disposed on opposite faces of a quartz crystal, such as an AT-cut crystal, as best shown in FIG. 2, which illustrates a cross-sectional view taken along line A-A of the sensing device depicted in FIG. 1. As will be explained in more detail hereinafter, the electrode 104, or a part thereof, can be fabricated from the selective material, in this case in the form of a layer, whereas the other electrode 102 and substrate 103 are fabricated from an inactive material such that the electrode 104 is selectively etchable by the etchant of interest.

Figure 3:
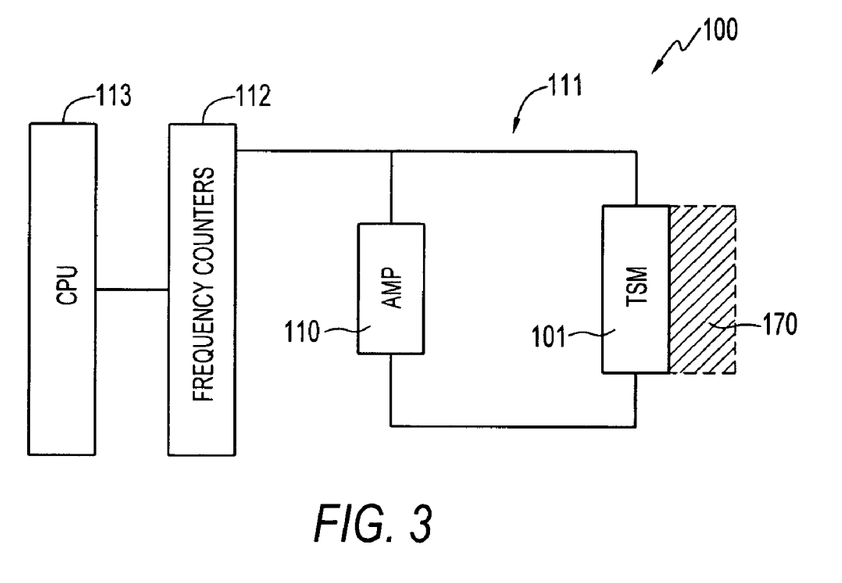
FIG. 3 illustrates a typical oscillation circuit of the sensor system including an amplifier and processing circuitry for analyzing the output response of the sensing device of FIG. 1.

Changes in the sensing device acoustic wave can be monitored by measuring the frequency of a stabilized oscillator formed by placing the sensing device 101 in the feedback loop of an amplifier, for example as shown in FIG. 3, which illustrates a typical oscillation circuit 111 of the sensor system 100 including an amplifier 110 and processing circuitry 112,113 for analyzing the output response of the sensing device 101 in contact with an etchant 170. The processing circuitry 112,113 consists of a frequency counter 112 and a computer processor unit (CPU) 113 electrically coupled to the amplifier 110.

The frequency of a thickness shear mode (TSM) crystal plate, such as an AT-cut plate, is inversely proportional to the thickness of the device. For example, a typical 5-MHz $3^{rd}$ overtone plate is on the order of 1 million atomic layers thick. Etching of the selective material equivalent to the mass of one atomic layer of quartz changes the frequency by about 1 ppm. Through calculations, it has been determined that the fundamental mode is nine times more sensitive than that of the $3^{rd}$ overtone. The crystal substrate of the sensing device of FIG. 1 can be typically a 5 MHz AT-cut TSM quartz crystal having a thickness of about 0.33 mm (fundamental). The thickness of the electrodes 102,104 is about 0.2-0.05 mm.

The change in frequency due to the selective layer material is typically determined by the following equation (1):

$$\Delta F = -2.3 \times 10^6 F^2 (\Delta M/A) \tag{1}$$

where the value $\Delta F$ represents the change in frequency due to the selective material layer (Hz), F represents the frequency of the quartz plate (Hz), $\Delta M$ represents the mass of deposited layer (g), and the value A represents the area coated by the layer (cm$^2$).

The reaction of the etchant, in this case, degraded engine oil, with the selective material of the electrode 104 effectively reduces the mass of the TSM resonator and consequently increases the resonant frequency of the resonator. The change in thickness of the electrode caused by etching over a given time period can be calculated theoretically using the aforementioned equation (1). The etch rate of the material will be equal to the change in thickness of the material divided by the etching time period. Alternatively, the sensing device can be calibrated manually by measuring experimentally the change in electrode thickness after etching the electrode for given period of time so as to correlate changes in oscillation frequency of the device with the etch rate of the electrode. The sensing device 101 can therefore provide an output response in which changes in the oscillation frequency of the sensing device acoustic wave caused by etching of the electrode 104 can be analyzed to evaluate the etching rate of the selective material.

Preferably, the selective material chosen to form the electrode 104 has a reduced reactivity such that reaction products produced at the surface of the selective material are removed by the etchant. By utilizing a selective material having a reduced reactivity, the etched surface remains fresh during sensor operation, that is, the etched surface remains free from reaction products, unlike in conventional corrosivity sensors in which metal oxide or metal sulfides remain on the electrode surface reducing the active surface of the sensor. Since the sensing device has a fresh surface for new reactions, the sensing device has a high sensitivity and a linear frequency response thoughout the life time of the sensor.

In this particular embodiment, the sensing system is designed for use in automotive applications in which the etchant is degraded engine oil which oil contains weak acids. The etchable electrode 104 for this application is fabricated by deposition of iron (Fe) onto the substrate 103. Iron (Fe) has a reduced reactivity with the acids contained in the engine oil such that reaction products, such as Fe$^{2+}$, are dissolvable in the oil. Furthermore, oxides which may form on the deposited iron due to air exposure prior to the sensing device being placed in contact with the oil, such as for example Fe$_2$O$_3$ or FeO, react with the acids in the oil in a similar manner as Fe. Other suitable reduced reactivity materials which may be utilized to fabricate the electrode 104 include iron (Fe), Nickel (Ni), manganese (Mn), cobalt (Co), chromium (Cr), vanadium (V), titanium (Ti), zinc (Zn), scandium (Sc), tin (Sn), magnesium (Mg) and Aluminum (Al). Or alternatively, metal alloys rich in one or more of these transition and non-transition metals.

In the arrangement shown in FIG. 1, the electrode 102 is fabricated from an inactive material, in this case, Au, so that the oil is unable to etch the electrode 102. Alternatively, the inactive material can be copper (Cu), mercury (Hg), platinum (Pt), palladium (Pd), silver (Ag), iridium (Ir) or other similar inactive metals. Also, metal-nonmetal compounds (e.g., ceramic based on TiN, CoSi$_2$, or WC) can form the inactive electrode. Alternatively, the sensing device can be designed such that, in operation, the etchant is unable to contact the other electrode 102 thereby rendering the electrode inactive. For example, the electrode 102 can be coated with a protective layer, such as an insulating layer, to seal the electrode from the etchant or the sensing device can be arranged such that only the selective material comes in contact with the etchant.

The electrodes 102,104 can be formed on the substrate 103 by various deposition techniques, for example by physical vapor deposition (PVD), chemical vapor deposition (CVD), sputtering or electro chemical deposition.

By preventing etching of the electrode 102, reduction of the Q factor and increase in motional resistance of the device is limited. Since the quartz substrate 103 is also inactive to the acids contained in the oil, the sensing device 101 is highly sensitive to the effects of the oil etching the electrode 104. Utilizing an etchable electrode and/or etchable substrate instead of inactive electrode 102 and substrate 103 is possible but results in a less sensitive device.

The method of operation of the sensor system 100 will now be described with reference to FIGS. 1-3. Initially, the sensing device 101 is placed in its operating position in which the electrode 104 is in contact with the etchant 170 of interest, in this case degraded engine oil. An oscillating acoustic shear wave is generated in the substrate 103 by applying an alternating voltage across electrodes 102,104. The resonant frequency is initially measured. The etchant reacts with the etchable electrode 104 causing the mass loading of the device to change and increasing the resonant frequency of the device over time. The resonant frequency of the device 101 is measured again after a given time period. The change in thickness of the selective material is calculated theoretically or experimentally as described hereinbefore. The etch rate of the selective material can be determined by dividing the change in thickness by the given time period.

Figure 4:
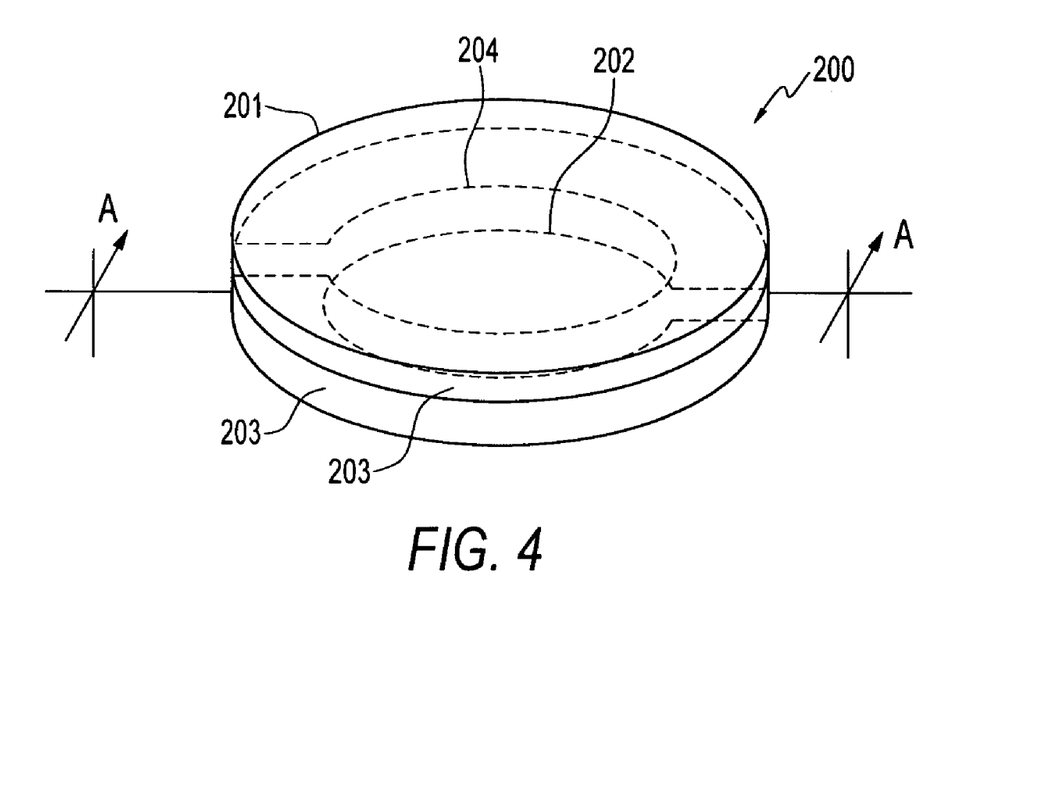
FIG. 4 illustrates illustrates a front perspective view of an acoustic wave sensing device of an etch rate sensor system in accordance with another embodiment.
Figure 5:
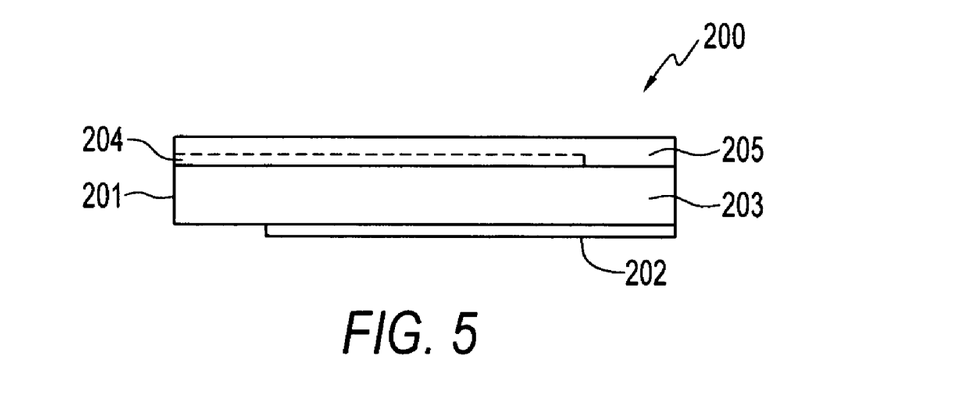
FIG. 5 illustrates a cross-sectional view taken along line A-A of the device of FIG. 4.

Referring to FIG. 4, which illustrates a front perspective view of an acoustic wave sensing system of an etch rate sensor system according to another embodiment, the sensor system 200 consists of an acoustic wave sensing device 201, which, like the device 101 of FIG. 1, is configured as a TSM resonator having a quartz substrate 203, such as AT-cut crystal, and a pair of electrodes 202,204 deposited on opposite faces of the substrate. However, as best shown in FIG. 5, which illustrates a cross-sectional view taken along line A-A of the device of FIG. 4, in this embodiment, the selective material, in this case Fe, is in the form of a layer or thin film 205 disposed on the substrate covering the electrode 204 such that the layer 205 rather than the electrode 204 is etchable by the etchant. The electrode 202 is formed from the inactive material, in this case gold Au or silver Ag. The electrode 204 is protected by the layer 205 and is, in this case, rendered unetchable by the etchant. Consequently, the electrode 204 need not be formed from an inactive material and can be formed from any material known in the art to be suitable for forming electrodes.

Figure 6:
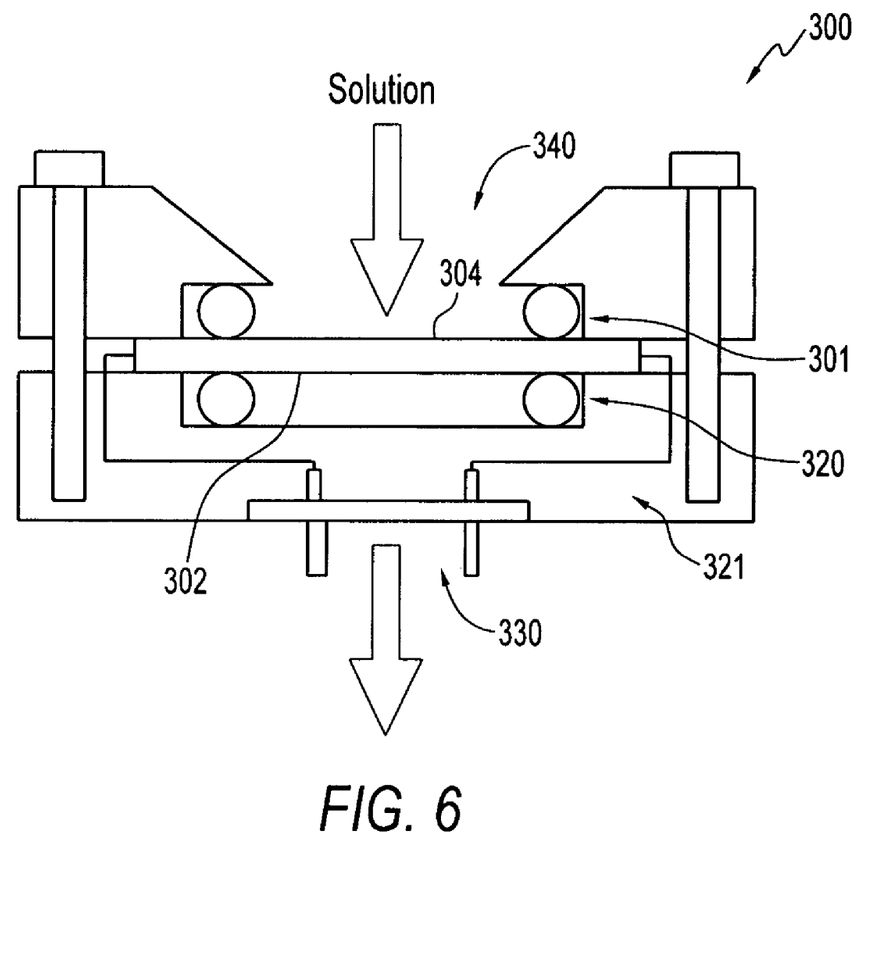
FIG. 6 illustrates a front perspective view of an acoustic wave sensor system for monitoring engine corrosion in accordance with another embodiment.

Reference will now be made to FIG. 6, which illustrates a front perspective view of an acoustic wave sensor system for monitoring engine corrosion according to another embodiment. In this embodiment the sensor system 300 is utilized in automotive applications to monitor engine wear caused by degraded engine oil corroding the engine. The system consists of an acoustic wave sensing device 301, configured as a TSM resonator similar to the resonator 101 shown in FIG. 1, mounted in a compartment 321 and sandwiched between a pair of o-rings 320. The compartment 321, which is adapted and arranged to be mountable in an oil filter system of a vehicle (not shown), has an inlet 340 for allowing oil to flow into the compartment in contact with the etchable electrode 304 of the sensing device and an outlet 330 for allowing oil to exit the compartment. The selective material which forms the etchable electrode 304 is chosen to have etching characteristics similar to, or the same as, the engine material such that the electrode 304 will be attacked by acids contained in the oil in the same manner as the engine itself. Consequently, this arrangement is particularly advantageous because the measurement of the change in thickness and/or etch rate of the selective material will provide a direct measure of the degree of engine corrosion caused by the oil as well as an indication of the level of degradation of the oil, i.e. the level of acid build up in the oil.

Figure 7:
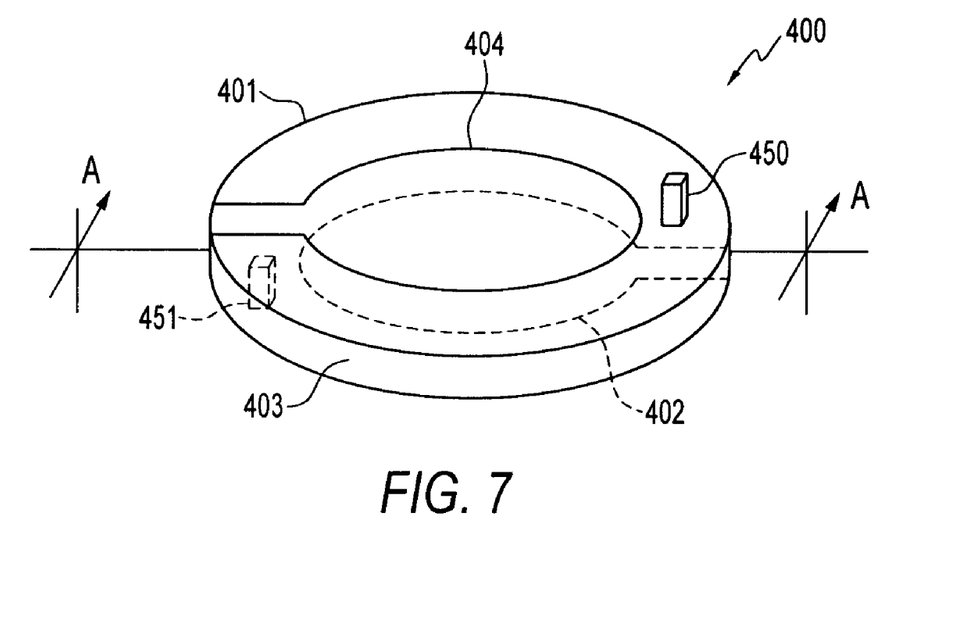
FIG. 7 illustrates a perspective view of a wireless acoustic wave sensing device of an etch rate sensor system in accordance with yet another embodiment.
Figure 8:
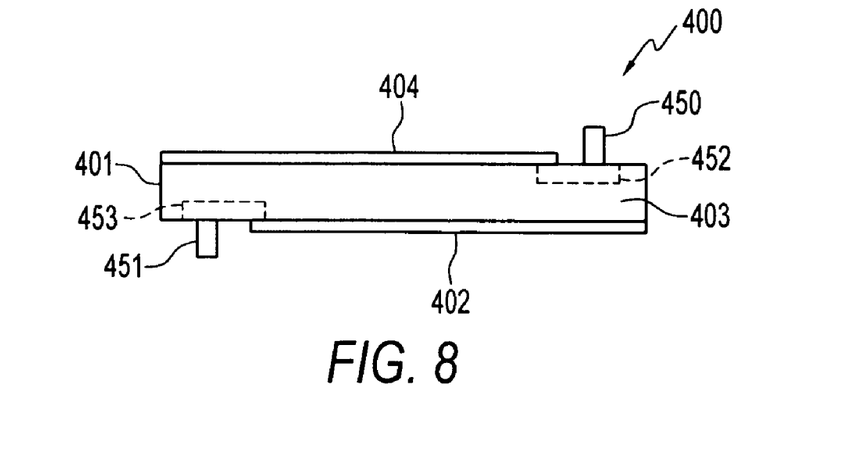
FIG. 8 illustrates a cross-sectional view taken along line A-A of the device of FIG. 7.

Referring to FIG. 7, which illustrates an acoustic etch rate sensor system having a wireless sensing device in accordance with yet another embodiment, a sensor system 400 has a sensing device 401 configured as a TSM resonator similar to the sensing device of FIG. 1 with the addition of an antenna 450,451 integrated in the device for receiving an interrogation signal. The sensor system 400 includes a reader or interrogation unit (not shown) for transmitting and receiving the interrogation signal. As shown in FIG. 8, which illustrates a cross-sectional view taken along line A-A of the sensing device of FIG. 7, in this embodiment, a pair of antennas 450,451 are disposed on the substrate 403 and are coupled to respective electrodes 404,402 via wireless components 452,453 such that the sensing device can transform the interrogation signal into the acoustic wave and provide the output response for transmission to the reader.

The interrogation signal can be a high frequency electromagnetic wave, such as an RF signal. The interrogation unit or reader interfaces amplifier and processing circuitry, for example as shown in FIG. 3, to the sensing device. Interrogation techniques or designs similar to those employed in radar applications can be used to transmit the interrogation signal and detect the output response, such as for example, time domain sampling using pulse radar, chirp radar designs or frequency domain radar using an FMCW or network analyzer structure designs. In automotive applications in which the sensing device is configured to be mounted in an oil filter system, such as for example like the sensing device 301 of FIG. 4, the interrogation unit and processing circuitry can be located in the control module of the vehicle.

By integrating the antenna 451, 450 into the sensing device 401, the sensing device is operable passively without the need for directly providing the sensing device with a power supply or oscillator. Furthermore, the sensor system 400 can detect and monitor the etch rate of the selective material remotely.

Figure 9:
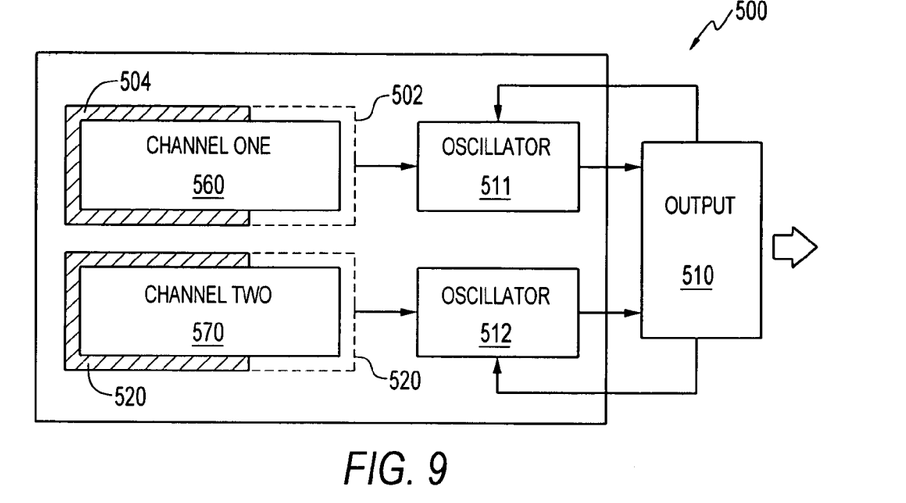
FIG. 9 illustrates a block diagram of a multiple mode acoustic wave sensor system, which can be adapted for use in etch rate sensing applications in accordance with an embodiment.

FIG. 9 illustrates a block diagram of a multiple mode acoustic wave sensor system 500, which can be adapted for use in etch rate sensing applications in accordance with an embodiment. System 500 can be implemented as a two-channel TSM resonator sensor, composed of a first channel 560 and a second channel 570. Each channel 560,570 includes a quartz crystal sensing component. First channel 560 is composed of an etchable electrode 504, fabricated from the selective material on the front face of the quartz crystal, and an inactive electrode 502 disposed on the rear face of the crystal. Second channel 570 includes a pair of inactive electrodes 520 disposed on respective front and rear faces of a quartz crystal. Second channel 570 includes a quartz crystal structure, which is identical to that contained by first channel 560, except for the etchable electrode 502. The two channels 560 and 570 can be placed in the feedback path of two identical oscillators 511 and 521, and the output 510 of the circuit is the difference of the two frequencies produced thereof. With this arrangement, the sensor system 500 can increase the sensing accuracy by eliminating response due to changes in the environment other than due to the etching of the selective material.

Frequency can be measured with far higher accuracy than any other quantity. Dual modes excitation such as that provided by apparatus 500 can provide superior sensing because the two modes occupy the same volume of quartz. In multiple modes excitation, the multiple excited modes occupy the same volume of piezoelectric material. Multiple modes can be excited simultaneously by means of multiple oscillator circuits sharing a common piezoelectric device.

Figure 10:
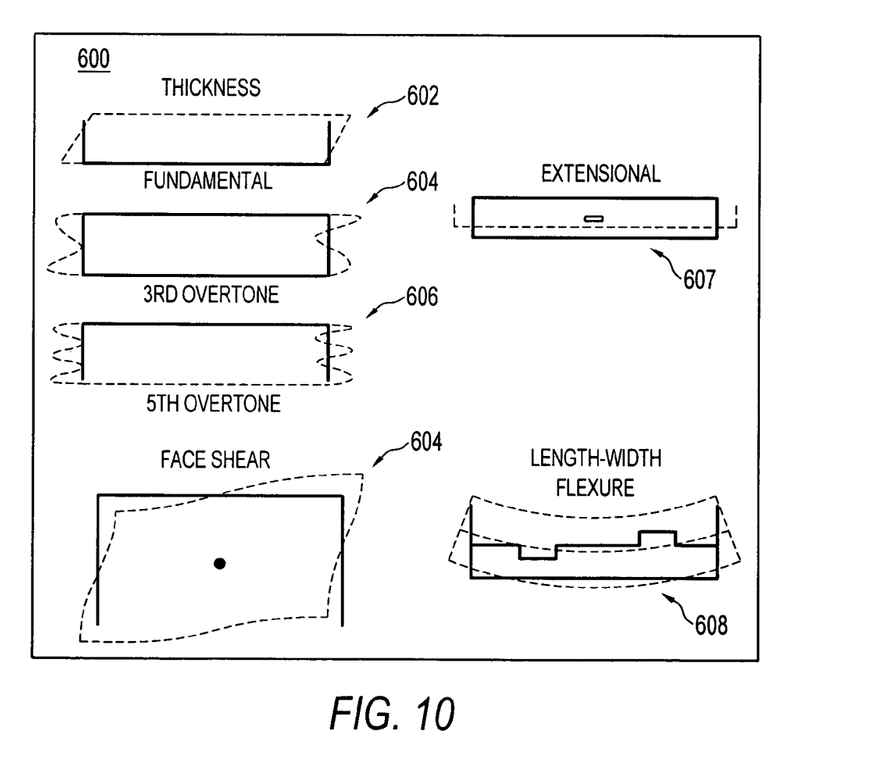
FIG. 10 illustrates a diagram depicting varying modes which can be utilized for etch rate sensors, in accordance with preferred or alternative embodiments.

FIG. 10 illustrates a diagram depicting varying modes 600, which can be utilized for etch rate sensors, in accordance with preferred or alternative embodiments of the present invention. For example, "thickness" is depicted in FIG. 10, including a fundamental 602, $3^{rd}$ overtone 604 and $5^{th}$ overtone 606. A face shear 604 is also depicted in FIG. 10, along with an extensional 607 and a length-width flexure 608. FIG. 10 illustrates the fact that many modes of vibrations can exist in an acoustic wave device, and that SAW and/or BAW devices are typically designed such that only one mode of vibration is optimized, while other modes are suppressed.

According to the embodiments described herein, such mode(s), can be utilized for etch rate type sensors. Such modes can include, for example, flexural plate mode (FPM) (e.g., see length-width flexure 608), shear-horizontal acoustic plate mode (SH-APM) (e.g., see face shear 604), and thickness shear mode (TSM) (e.g., see fundamental 602, $3^{rd}$ overtone 604 and $5^{th}$ overtone 606). It can be appreciated of course that such modes are only a few of many other types of modes which can be utilized in accordance with preferred or alternative embodiments, and are referred to herein for illustrative purposes only.

Figure 11:
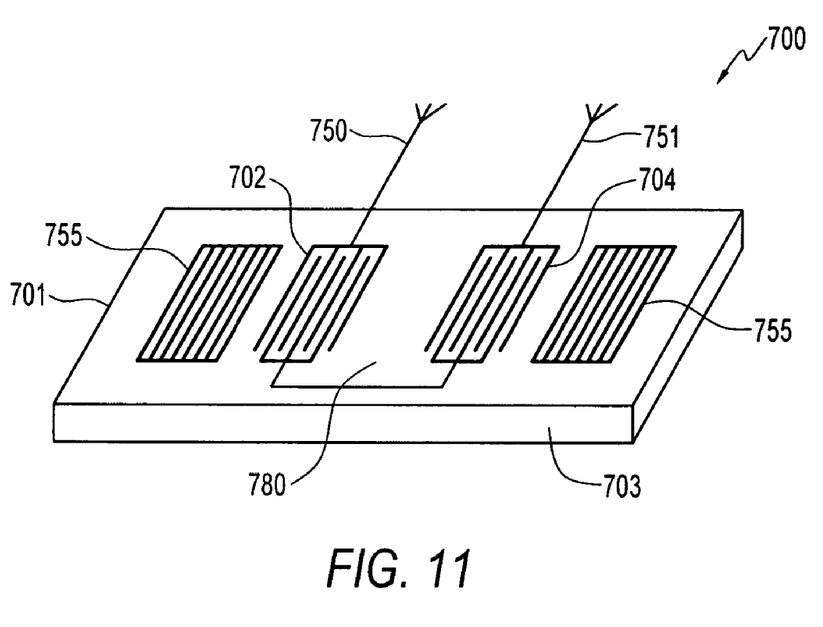
FIG. 11 illustrates a perspective view of an acoustic etch rate sensor system having a passive acoustic SH-SAW sensing device in accordance with an embodiment.

For example, an embodiment of the sensor system having a passive acoustic wave SH-SAW sensing device is illustrated in FIG. 11. The sensing device 701 has electrodes in the form of interdigital transducers (IDTs) 702,704 disposed on an upper surface of a quartz substrate 703 which IDTs are electrically coupled to respective antennas 750, 751 extending on and away from the substrate 703. The antennas 750, 751 can be, for example, a linear type antenna, or a coupler type antenna depending upon design considerations. In this embodiment, the antennas are 2 half pair antennas. Alternatively, other antennas, such as for example loop or slot-type, can be used.

The input and output IDTs are each arranged in a 2.5 finger-pair configuration and are located in parallel between a pair of reflectors 755, separated by 20 wavelengths ($\lambda$), which reflectors are arranged to reflect at least part of the propagating wave back to a resonator cavity 780 located between the input and output IDTs 702, 704. In this case, each reflector consists of about 200 reflecting members, such as aluminum stripes, and each member is 40 $\lambda$ in length. The center frequency of the device is about 40 MHz.

IDT 704 is fabricated from the selective material, for example Fe, such that the IDT 704 is etchable by the etchant whereas IDT 702, and reflectors 755 are coated with a thin insulating film, such as for example a 50 A Amstrong thick layer of aluminum oxide ($Al_2O_3$), in order to protect them from the oil or other etchant.

The sensing device 701 is arranged such that an interrogation signal is transformed by the input transducer 702 into a shear-horizontal acoustic wave (SH-SAW) which propagates on the substrate surface. Changes to the wave caused by the etchant etching the IDT 704 are sensed by the output IDT 704 and a response of the output IDT is transmitted by the antenna 751 for remote analysis of these changes to evaluate the change in thickness and/or etch rate of the selective material.

Other examples of sensing device configurations include, inter alia, SH-APM devices and FPM devices. SH-APM can use thin quartz plates that serve as acoustic wave-guides, confining acoustic energy between the upper and lower surfaces of the plate as a wave propagates between input and output transducers unlike in a SAW device in which almost all acoustic energy is concentrated within the wavelength of the surface. The consequences of this difference are that the sensitivity of the SH-APM to mass loading and other perturbations depends on the thickness of the quartz. Both surfaces of the device undergo displacement, so the detection can occur on either surface of the device.

A number of advantages can be obtained through the use of FPW devices. For example, the detection sensitivity is not based on frequency of operation like other acoustic devices, but instead on the relative magnitude of the perturbation to a parameter of the membrane. In the case of mass, the sensitivity is the ratio of the added mass to the membrane mass. Since very thin (low mass) membranes can be created, the detection sensitivities can be very large, much larger than other acoustic sensor modes. Frequencies of operation are in 100's of kHz to few MHz range. The low operating frequency leads to simple electronic circuits to drive and detect sensor signals.

For example, when the sensing device is configured as a SAW, SH-APM, FPM or other type of resonator, the resonator can be configured as a two-port resonator, i.e., a filter, in which an input interdigital transducer (IDT) and an output IDT are formed on the substrate between a pair of reflectors. A selective layer can be disposed on the substrate or alternatively, one of the IDTs or reflectors can be made selective. The selective sensitive layer can cover and protect the electrodes and reflectors and/or can be disposed between the two IDTs.

Each reflector may comprise at least one metallic membrane, such as metallic stripe, if necessary made from the selective material, and formed on the substrate spaced from the IDT(s). Alternatively, the inactive reflector may comprise an edge of the substrate which edge is substantially perpendicular to the propagation path of the wave.

The embodiments and examples set forth herein are presented to best explain the present invention and its practical application and to thereby enable those skilled in the art to make and utilize the invention. Those skilled in the art, however, will recognize that the foregoing description and examples have been presented for the purpose of illustration and example only. Other variations and modifications of the present invention will be apparent to those of skill in the art, and it is the intent of the appended claims that such variations and modifications be covered.

The description as set forth is not intended to be exhaustive or to limit the scope of the invention. Many modifications and variations are possible in light of the above teaching without departing from the scope of the following claims.

For example, the skilled person would understand that the sensor system can be utilized to measure ethants other than the oil etchants described herein with reference to the embodiments.

Additionally, the skilled person would understand that techniques for measuring propagating wave characteristics other than the frequency measuring technique described herein with reference to the embodiments can be utilized to monitor the etching characteristics of the selective material. For example, techniques to measure the phase or velocity change of the propagating wave caused by etching the selective material can be used such as direct phase measurement, which involves directly comparing the transfer phase to some reference phase, or a sing around arrangement which involves measuring a pulse rate obtained when a pulse detector at the output IDT of a delay line triggers the next pulse at the input IDT.

It is contemplated that the use of the present invention can involve components having different characteristics. It is intended that the scope of the present invention be defined by the claims appended hereto, giving full cognizance to equivalents in all respects.

The embodiments of the invention in which an exclusive property or right is claimed are defined as follows. Having thus described the invention what is claimed is:

1. An acoustic wave sensor system for monitoring the etchability of a material exposed to an etchant, the sensor system comprising:
    an acoustic wave sensing device having
        a piezoelectric substrate, and
        a pair of electrodes, coupled to said substrate, said pair of electrodes being adapted and arranged to generate an acoustic wave propagating in the device upon application of a voltage potential and to transform the propagating wave into an output response,
        a selective material disposed on said substrate, said material being chemically reactive with said etchant such that said material is etchable by said etchant,
        wherein one of said electrodes is at least partially formed from said selective material or has said selective material disposed thereon, and
        wherein the other of said electrodes is made inactive to said etchant; and at least one reflector for reflecting the propagating wave back to at least one electrode;
    whereby, said sensing device can provide an output response in which changes in frequency, phase or other propagation characteristics of said wave caused by etching of said selective material can be analyzed to evaluate the etching rate or etchability of said selective material.

2. The sensor system of claim 1, wherein said selective material has a reduced chemical reactivity such that reaction products produced at an etched surface of said selective material are removed by said etchant thereby leaving said surface clean for subsequent sensing.

3. The sensor system of claim 2, wherein said selective material comprises a metal element or a metal alloy containing said metal element.

4. The sensor system of claim 1, wherein said other electrode is formed from an inactive material or coated with a protective layer to make said other electrode inactive to said etchant.

5. The sensor system of claim 1, wherein at least one of said reflectors is at least partially formed from the selective material such that a reflector thereof is etched by the etchant.

6. The sensor system of claim 1, wherein said sensing device further comprises a layer disposed on said substrate, said layer being fabricated from said selective material.

7. The sensor system of claim 1, wherein said sensing device is configured as an acoustic wave resonator, an acoustic wave filter or as an acoustic wave delay line device.

8. The sensor system of claim 1, wherein said sensor system further comprises an antenna, integrated in said sensing device, for receiving an interrogation signal and/or for transmitting the sensing output response.

9. The sensor system of claim 1, wherein sensing device is configured as a shear mode surface acoustic wave mode device (SH-SAW).

10. An acoustic wave sensor system for monitoring engine corrosion, the sensor system comprising:
an acoustic wave sensing device having
a piezoelectric substrate,
a pair of electrodes coupled to said substrate between a pair of reflectors, said pair of electrodes being adapted and arranged to generate an acoustic wave propagating in the device upon application of a voltage potential and to transform the propagating wave into an output response, and
a selective layer of material disposed on said substrate and having a chemical reactivity such that the selective layer is etchable by degraded engine oil,
wherein one of said electrodes/reflectors is at least partially formed from said selective material or has said selective material disposed thereon, said selective layer comprising a metal element or a metal alloy containing said metal element, the chemical reactivity of the layer with said oil being such that reaction products produced at an etched surface of the layer are removed by said etchant;
wherein the other of said electrodes/reflectors is made inactive to said etchant, and
whereby, said sensing device can provide an output response in which changes in frequency, phase or other propagation characteristics of said wave caused by etching of said selective layer can be analyzed to evaluate the etching rate of the selective layer and thereby monitor the degree of engine corrosion caused by said degraded oil.

11. The system of claim 10, wherein said selective layer has etching characteristics similar to or the same as the engine.

12. The sensor system of claim 10, wherein said selective layer comprises at least one of the following metal elements: iron (Fe), Nickel (Ni), manganese (Mn), cobalt (Co), chromium (Cr), vanadium (V), titanium (Ti), zinc (Zn), scandium (Sc), tin (Sn), magnesium (Mg) and Aluminum (Al).

13. The sensor system of claim 10, wherein said selective layer at least partially forms an electrode.

14. The sensor system of claim 10, wherein said piezoelectric substrate comprises a quartz crystal.

15. The system of claim 10, further comprising
an engine oil filter system, said acoustic wave sensing device being mounted in said engine oil filter system.

16. A method of sensing the etch rate of a selective material comprising:
generating an acoustic wave
propagating said acoustic wave in a piezoelectric substrate having a pair of electrodes and at least one reflector disposed thereon,
reflecting the propagating wave back to at least one electrode;
making one of said electrodes inactive to an etchant,
forming said other electrode from a selective material or disposing said selective material thereon;
etching said selective material
transforming said propagating wave into an output response, and
analyzing said output response to measure changes in the frequency, phase or other propagation characteristics of said wave caused by said etching.

17. The method of sensing of claim 16, wherein the step of etching said selective material comprises:
exposing said selective material to engine oil contained in an oil filter system for filtering oil from an engine.

18. The method of claim 17, further comprising:
selecting said selective material such that said material has etching characteristics similar to or the same as said engine.

* * * * *